United States Patent [19]

Wolff

[11] Patent Number: 4,642,318

[45] Date of Patent: Feb. 10, 1987

[54] METHOD FOR DECREASING RADIATION LOAD IN PUVA THERAPY

[76] Inventor: Klaus Wolff, Patscherstrasse 7, A-6080 Igls, Austria

[21] Appl. No.: 747,549

[22] Filed: Jun. 21, 1985

Related U.S. Application Data

[63] Continuation of Ser. No. 442,362, Nov. 17, 1982, abandoned, which is a continuation of Ser. No. 119,619, Feb. 8, 1980, abandoned, which is a continuation of Ser. No. 856,069, Nov. 30, 1977, abandoned.

[51] Int. Cl.$^4$ .......................... A01N 37/08; A61N 5/12
[52] U.S. Cl. ...................................... 514/560; 128/1.1; 514/725; 514/863
[58] Field of Search ...................... 128/2, 1.1; 514/560, 514/725, 863

[56] References Cited

U.S. PATENT DOCUMENTS

| | | | |
|---|---|---|---|
| 3,931,257 | 1/1976 | Pawson | 260/326.43 |
| 3,934,028 | 1/1976 | Lee | 514/560 X |
| 3,966,967 | 6/1976 | Lee | 514/560 X |
| 4,055,659 | 10/1977 | Ganders et al. | 260/410.5 |

FOREIGN PATENT DOCUMENTS

| | | | |
|---|---|---|---|
| 818648 | 2/1975 | Belgium | 514/560 |
| 833784 | 4/1976 | Belgium | 514/560 |
| 2300107 | 7/1974 | Fed. Rep. of Germany | 514/560 |
| 2306112 | 8/1974 | Fed. Rep. of Germany | 514/560 |
| 2440606 | 3/1975 | Fed. Rep. of Germany | 514/560 |
| 2440525 | 3/1975 | Fed. Rep. of Germany | 514/560 |
| 2542600 | 4/1976 | Fed. Rep. of Germany | 514/560 |
| 2542601 | 4/1976 | Fed. Rep. of Germany | 514/560 |
| 7404324 | 10/1974 | Netherlands | 514/560 |

OTHER PUBLICATIONS

Stegmaier Journal of Investigative Dermatology, 1959, vol. 32, pp. 345 to 349.

*Primary Examiner*—Dale R. Ore
*Attorney, Agent, or Firm*—Jon S. Saxe; Bernard S. Leon; Richard J. Mazza

[57] ABSTRACT

The total radiation load on a subject being treated for psoriasis with a psoralen in conjunction with ultraviolet A radiation (PUVA) can be substantially reduced by at least pretreating said subject with an anti-psoriatic effective polyene compound such as a retinoid, β-carotene or phytoene.

12 Claims, No Drawings

METHOD FOR DECREASING RADIATION LOAD IN PUVA THERAPY

This is a continuation of application Ser. No. 442,362, filed Nov. 17, 1982, abandoned, which is a continuation of application Ser. No. 119,619, filed Feb. 8, 1980, abandoned, which is a continuation of application Ser. No. 856,069, filed Nov. 30, 1977, abandoned.

BACKGROUND OF THE INVENTION

A major breakthrough in the treatment of psoriasis has been the discovery that a regimen involving systemic treatment with a psoralen derivative such as orally administered 8-methoxypsoralen followed in two to five hours by exposure of the subject to ultraviolet A light resulted in an extremely high clearing response rate of the psoriatic lesions.

Regimens which have been utilized in a multi-center clinical trial of this treatment procedure involve two to four times per week treatments during the clearing phase which ranged from an average of 20 to 77 days depending on treatment frequency and patient's skin color. Upon complete clearing the subject received maintenance treatments consisting initially of one to three treatments per week which gradually tapered to about once a month.

The oral dosage levels used in the aforesaid studies were based on the patient's weight: up to 50 kg. body weight, 20 mg.; 51–65 kg., 30 mg.; 66–80 kg., 40 mg.; greater than 80 kg., 50 mg. Total energy applied to the subjects using ultraviolet A light exposure during the clearing phase therapy ranged from an average of approximately 90 Joules/cm$^2$ to over 200 Joules/cm$^2$ depending at least in part on the drug dosage regimen utilized.

Further specific details concerning the methodology of the PUVA treatment for psoriasis are to be found in U.S. Patent Application Ser. No. 618,152, filed Sept. 30, 1975, entitled "Process for Artifically Inducing a Natural Tan of the Human Body and Alleviating Psoriasis", inventors Thomas B. Fitzpatrick and John A. Parrish.

In U.S. Patent Application Ser. No. 823,257 filed Aug. 10, 1977, entitled "Process to Produce 8-Methoxypsoralen and Derivatives Thereof", inventors P. N. Confalone et al., there are disclosed analogs of 8-methoxypsoralen which exhibit potent photosensitizing activity which is thought to be linked to antipsoriatic activity. Such analogs are 2-methyl-9-methoxypsoralen, 5-methyl-9-methoxypsoralen and 2,5-dimethyl-9-methoxypsoralen.

Additional psoralen derivatives exhibiting potent photobiological activity are disclosed by Issacs et al., Biochemistry, 16, 1058 (1977). Particular new psoralen derivatives disclosed include 4′-hydroxymethyl-,4′-methoxymethyl-, and 4′-amino-methyl-4,5′,8-trimethylpsoralen. Furthermore, D. Averback has reported recently that a newly synthesized psoralen 3-carbethoxypsoralen is a potent photoactive derivative. See VII International Congress on Photobiology Aug. 29–Sept. 3, 1976) at page 137.

Anti-psoriatic polyene compounds are known in the prior art. Examples of such disclosures are as follows:

Belgian Pat. No. 833,784 (Derwent 26452X)—Phenyl-tetraene compounds such as 9-phenyl-3,7-dimethyl-nona-2,4,6,8-tetraen-1-oates.

Belgian Pat. No. 818,648 (Derwent 14330W)—Fused carbocyclic-substituted polyenes such as 9-(8-methoxy-6,7-dimethyl-tetralin-5-yl)-3,7-nona-2,4,6,8-tetraen-1-oic acid and its esters as well as 2,3-dimethyl-naphthalene and pentamethylchromanyl derivatives.

Netherlands Pat. No. 7404324 (Derwent 73782V)—Polyene compounds such as 9-(4-methoxy-2,3,6-trimethylphenyl)-3,7-dimethyl-nona-2,4,6,8-tetraenic-1-carboxylic acid.

U.S. Pat. No. 3,931,257 (Derwent 05421X)—Substituted nona-2,4,6-trienoic acid derivatives such as 3,7-dimethyl-9-(2,6,6-trimethyl-cyclohex-1-en-1-yl)-nona-2,6,8-trien-1-oic acid methyl ester.

West German Pat. No. 2542600 (Derwent 32296X)—Halo substituted polyene compounds such as 3,7-dimethyl-9-(2-chloro-4-methoxy-3,5,6-trimethylphenyl)-nona-2,4,6-trienoic-1-acid, 3,7-dimethyl-9-(2,3,4,5,6-pentachlorophenyl)-nona-2,4,6-trienoic-1-acid and esters thereof.

West German Pat. No. 2542601 (Derwent 32297X)—9-Aryl polyenes such as 9-aryl-3,7-dimethyl-nona-2,6,8-trien-1-oic acids and derivatives.

West German Pat. No. 2440525 (Derwent 17939W)—Dihydro-vitamin A derivatives and analogs which are substituted in the 2- and 6-position by lower alkyl, lower alkoxy or halogen and in more than one of positions 3,4 and 5 by hydroxy, halogen, lower alkyl, lower alkenyl, lower alkoxy, lower alkenoxy, lower alkanoyloxy, amino or N-heterocyclic residue. An exemplary compound is 2-cis/trans-3,7-dimethyl-9-(2,6,6-trimethyl-1-cyclohexenyl)-nona-2,4,6-trienoate.

West German Pat. No. 2440606 (Derwent 17953W)—Dihydrovitamin A derivatives and analogs including, for example 3,7-dimethyl-9-(2,6,6-trimethylcyclohex-1-en-1-yl)-nona-2,6,8-trien-1-oic acid, 3,7-dimethyl-9-(4-methoxy-2,3,6-trimethylphenyl)-nona-2,6,8-trien-1-oic acid and esters thereof.

Belgian Pat. No. 813002 (Derwent 74285V)—Substituted phenyl-nona-tetraenic acids, esters and amides including, for example butyl 9-(4-methoxy-2,3,6-trimethyl-phenyl)-3,7-dimethyl-nona-2,4,6,8-tetraen-1-oate and the corresponding ethyl ester.

West German Pat. No. 2306112 (Derwent 60135V)—N-substituted thiourea derivatives of vitamin A acid.

West German Pat. No. 2300107 (Derwent 52199V)—N-substituted vitamin A acid amides.

Belgian Pat. No. 847943 (Derwent 32747Y) — Esters and amides of all trans retinoic acid such as retinoyloxyacetamide.

U.S. Pat. No. 3,934,028—Use of retinoic acid analogs in the treatment of acne and psoriasis. A specific compound disclosed is 11-(2,6′,6′-trimethylcyclohex-1-enyl-1′)-5,9-dimethylundeca-2,4,6,8,10-pentenoic acid.

U.S. Pat No. 3,966,967—Use of vinylogs of retinoic acid to treat psoriasis and related skin disorders. A specific compound disclosed is 2,6,6-trimethyl-1-(10′-carboxy-deca-1′,3′,5′,7′,9′-pentaenyl)cyclohex-1-ene.

DESCRIPTION OF THE INVENTION

The present invention relates to an improved method for the treatment of psoriasis whereby the radiation load on a subject undergoing therapy with a psoralen in combination with ultraviolet A radiation can be substantially reduced by pretreatment with a polyene compound having anti-psoriatic activity.

Suitable polyene compounds used in the method of the present invention include retinoic acid derivatives and analogs, β-carotene, phytoene and similar compounds which are known in the art to have antipsoriatic activity. Preferred compounds in accordance with this invention are retinoic acid derivatives and analogs, particularly all trans-9-(4-methoxy-2,3,6-trimethylphenyl)-3,7-dimethyl-2,4,6,8-nonatetrene-1-oic acid esters. A most preferred compound is ethyl all trans-9-(4-methoxy-2,3,6-trimethylphenyl)-3,7-dimethyl-2,4,6,8-nonatetraenoate.

The treatment with aforesaid preferred polyene compounds is initiated prior to the start of the PUVA therapy, usually about 4 to 10 days, preferably 7 days before. The subject is given the polyene compound in its usual anti-psoriatic mode of administration. Thus, for example, with a preferred polyene, ethyl all trans-9-(4-methoxy-2,3,6-trimethylphenyl)-3,7-dimethyl-2,4,6,8-nonotetraenoate, the pretreatment will involve enteral or parenteral administration in daily doses of 5–200 mg. A preferred form is a capsule containing 10–100 mg. Forms suitable for topical administration include solutions containing 0.1 to 0.3% of active compound, pommades and creams containing 0.05–5% of active compound.

Upon completion of the initial polyene treatment conventional therapy with a psoralen compound in combination with ultraviolet A radiation (PUVA) of from wavelength of 3200 to 4000 angstroms can be started. The polyene treatment can be maintained concurrently with the PUVA treatment on a daily basis or on those days when PUVA is being administered (one to three times weekly). Alternatively, the polyene treatment can be stopped during the clearing phase therapy.

By utilizing the improved method of the present invention during the clearing phase it is possible to shorten the total duration of the PUVA treatment, to reduce the number of irradiations and most importantly to substantially reduce the total UV energy applied to achieve clearing. The reduction in radiation load on a psoriatic patient undergoing PUVA treatment is an extremely valuable advance in the art since one of the imponderable side effect risks of PUVA treatment is the possible induction of skin cancers. Such risk is difficult to assess in reasonable clinical trials due to the extremely long latency period of such cancers which can occur ten, twenty or even a greater number of years after treatment. Reduction of the total radiation load on the subject in accordance with the method of this invention will substantially decrease the risk of potential future carcenogenicity, thereby enhancing the safety of a procedure which has already been shown to be efficacious in extensive clinical trials.

The psoralen which is employed in the PUVA therapy can be any of the psoralens which have been shown in the prior art to exhibit strong photobiological activity. A particularly preferred psoralen is 8-methoxypsoralen, also known as methoxsalen.

The present invention is further illustrated by the following examples.

EXAMPLE 1

The regimen involving pretreatment of psoriatic subjects with a polyene compound, ethyl all trans-9-(4-methoxy-2,3,6-trimethylphenyl)-3,7-dimethyl-2,4,6,8-nonatetraenoate, followed by standard PUVA treatment utilizing methoxsalen was tested in a clinical trial. Results obtained were matched against prior clinical test data obtained for the standard PUVA treatment. Protocols for each of the regimens employed in these tests are summarized below.

STANDARD PUVA PROTOCOL

Fifty-nine patients were subjected to standard PUVA therapy according to techniques described previously, see for example Wolff et al., Brit. J. Dermatol. 96, 1 (1977). This consisted of the oral administration of methoxsalen at a dose of 0.6 mg/kg per body weight followed after a two hour interval by irradiation with a high energy output UVA light source. UVA dosimetry was based on the results of phototoxicity testing in which test areas on previously non-sun exposed sites of the body are exposed to increasing doses of UVA energy two hours after the patient had ingested 0.6 mg/kg body weight of methoxsalen. Erythema reactions which develop after such exposures are read after three days and the light dose which produced a barely visable erythema is designated as minimal phototoxicity dose (MPD). This dose is employed as the initial dose in the treatment and is later on increased as the patient develops pigmentation. Both the testing procedures and the parameters for adjusting and increasing UVA energy doses in subsequent treatments have been described in detail in the literature. Treatments were given four (4) times a week and were continued until complete clearing of all lesions had occurred. Patients were then continued on a standard maintenance regimen which consisted of one to two treatments per week which were gradually tapered to about once per month.

POLYENE PRETREATMENT SUBGROUP I PROTOCOL

Twenty-seven patients with severe generalized plaque psoriasis were given oral ethyl all-trans-9-(4-methoxy-2,3,6-trimethylphenyl)-3,7-dimethyl 2,4,6,8-nonatetraenoate (polyene) as a total daily dosage of 1 mg/kg body weight usually in three to four divided doses. After four days standard PUVA therapy as described above was added to this regimen and this combined treatment was continued until full clearing of all lesions was achieved, the longest being 24 days. At this point, polyene treatment was stopped and patients were continued with maintenance PUVA treatment as described above.

POLYENE PRETREATMENT SUBGROUP 2 PROTOCOL

Nine patients with generalized plaque type psoriasis received polyene compound at a total daily dose of 1 mg/kg body weight in three to four divided doses and this treatment was continued for seven to ten days. At this time, standard PUVA therapy as described above was added to the regimen and the combined treatment was continued until full clearing of lesions was achieved in all patients. At this point, polyene treatment was again stopped and patients entered the maintenance treatment phase with PUVA alone as outlined above.

PALMOPLANTAR PSORIASIS PROTOCOL

Twelve patients with severe recalcitrant palmoplantar psoriasis resistant to conventional therapy received the polyene compound at a total daily dose of 1 mg/kg body weight usually in three to four divided doses. After four days, standard PUVA therapy was initiated and the combined treatment was continued until a complete clearing of lesions was achieved. Polyene treatment was then stopped and patients entered maintenance treatment phase was PUVA alone as the other subgroups tested.

PUVA FAILURE PROTOCOL

Eleven patients with severe recalcitrant psoriasis who had been treated with standard PUVA therapy for prolonged periods of time (up to 28 irradiations) without reaching complete clearing, and seven additional patients who, after initial clearing with PUVA developed severe relapses requiring so many maintenance treatments that they had to be treated from three to four times per week and, thus, had to be considered maintenance treatment failures, were also studied. Most of these 18 patients were deeply tanned and required very high doses of light energy per treatment (up to 25 joules per centimeter square). In these patients, treatment with polyene compound was added to the conventional PUVA treatment regimen and patients received total daily doses of 1 mg/kg body weight. Both treatments were continued until full clearing was achieved and polyene treatment was then withdrawn. Patients were then continued on a regular maintenance PUVA therapy regimen as outlined above.

The results obtained from such trials are summarized below in Tables 1 and 2.

TABLE 1

Clearing Phase Therapy:
Polyene regimen compared to standard PUVA regimen

| | Duration of PUVA treatment (days) | Irradiations | Total energy applied (Joules/cm$^2$) |
|---|---|---|---|
| Standard PUVA (n = 59) | 27.8 ± 15.2 | 14.3 ± 7.8 | 93.2 ± 80.6 |
| Polyene Plaque-type psoriasis subgroup 1 (n = 27) | 17.3 ± 7.6 | 9.7 ± 4.1 | 36.2 ± 33.0 |
| Polyene Plaque-type psoriasis subgroup 2 (n = 9) | 11.0 ± 6.7 | 6.3 ± 3.5 | 22.6 ± 31.2 |
| Polyene Palmoplantar psoriasis subgroup 3 (n = 12) | 12.8 ± 5.5 | 7.0 ± 3.0 | 21.4 ± 17.3 |

TABLE 2

Clearing and maintenance phase failures (PUVA):
Response to Polyene Regimen

| Full clearing achieved after (irradiations) | Number of Patients |
|---|---|
| up to 4 | 4 |
| 4-8 | 7 |
| 8-12 | 2 |
| 12 or more | 5 |

Patients treated with the standard PUVA protocol above, responded in the usual manner and clearing was achieved in 28 days (mean) requiring 14 irradiations (mean) and a total energy of long wave ultraviolet light of 93 joules per centimeters square (mean). In contrast, clearing was achieved much faster in Subgroup I requiring only 17.3 days (mean) and 9.7 irradiations (mean). This represents a decrease of approximately 30% of the duration and the number of treatments of standard PUVA therapy and is statistically highly significant (p smaller than 0.01). The total cumulative dose of UVA energy applied was reduced by ¼ in Subgroup I as compared to standard PUVA therapy and again this is statistically highly significant (p smaller than 0.01).

In Subgroup 2, complete clearing of psoriatic lesions was obtained within 11 days (mean) requiring 6.3 (mean) irradiations. This represents a more than 50% reduction of treatment time and number of irradiations of the treatment time and irradiations of standard PUVA therapy. The duration of treatment in Subgroup 2 is also significantly shorter than in Subgroup I (11 versus 17.3 days and 6.3 versus 9.7 irradiations) and is statistically significant (p smaller than 0.05). The amount of UVA energy required to achieve complete clearing in Subgroup 2 was significantly reduced to 22.6 joules per centimeter square and represented only approximately 25% of that required by standard PUVA therapy.

Patients with palmoplantar psoriasis responded dramatically. Complete clearing was achieved with as little as 7 irradiations (mean) in 12.8 days (mean) and this was also better than in the patients with plaque type psoriasis in Subgroup I.

In the clearing and maintenance phase failure study (Table 2) outpatients previously resistant to standard PUVA therapy were brought to full clearing when polyene was added to the regimen and in most cases with reasonably few PUVA treatments. In four patients, only 4 irradiations were required to achieve clearing, in seven — 4 to 8 treatments, in two — 8 to 12 PUVA treatments, and only in five — 12 or more PUVA treatments were required to achieve these results.

The therapeutic principle presented in this application is based on an enhancement of the beneficial effects of PUVA by an additional chemotherapeutic agent of different pharamacologic properties (polyene compound). The results presented show that this conjunctive therapy has three (3) main advantages over standard PUVA therapy: (1) conjunctive therapy decreases the total energy of UVA required for clearing by PUVA, (2) it accelerates the response rate of psoriasis to PUVA treatment, and (3) it succeeds where PUVA fails. Polyene compounds, thus, appear to be potent accelerators of PUVA therapy. The number of irradiations can be cut by one third or even by more than one half as shown in Subgroup 2 and both the duration of the individual treatments and the length of the total treatment time are shortened. Most important, however, is the fact that the total cumulative doses of UVA energy necessary for clearing can be reduced to roughly one fourth of what would be required by conventional PUVA therapy, as clearing is reached in most patients before a deep tan necessitates a substantial increase of irradiation doses. Patients receiving conjunctive therapy can be dismissed into maintenance phase of PUVA therapy with low energy requirements per exposure. These patients can be kept under control by standard maintenance PUVA treatment as effectively as those cleared with standard PUVA alone and since smaller UVA doses are required in the maintenance PUVA regimen these results show an even more dramatic reduction of cumulative energy doses in long term maintenance treatments. It can, therefore, be predicted that potential long term hazards of PUVA therapy, notably degenerative and oncogenic changes of the skin which are presumably related to the total cumulative UVA energy dose, will be considerably lessened.

Also, patients who represent clearing and maintenance failures of conventional PUVA therapy similarly benefit from conjunctive treatment. The addition of polyene compound to the treatment regimen converts seemingly PUVA resistant cases to responders. Patients who require exceedingly high doses of energy and frequent exposures of PUVA maintenance therapy, therefore, benefit from this conjunctive treatment regimen.

This regimen also appears suited for patients with severe psoriatic flares and high energy requirements for maintenance and for patients who, after initial clearing, develop localized recalcitrant psoriatic lesions not as readily amenable to standard PUVA therapy.

In summary, conjunctive therapy with polyene and PUVA decreases the total energy of UVA required for PUVA by up to 75%, it accelerates the response rate of psoriasis to PUVA by 40% to 60%, and it succeeds where PUVA fails. Conjunctive therapy is, therefore, far more effective than PUVA and since it reduces energy requirements of PUVA therapy it diminishes the likelihood of potential of long term hazards of this treatment.

EXAMPLE 2

Tablet Formulation — Psoralen

Psoralen Compound: 20.4 grams
Polysorbate 80: 1.0 grams
Microcrystalline Cellulose $PH_{101}$: 40.0 grams
Corn Starch, USP: 25.0 grams
Magnesium Stearate: 1.6 grams
Lactose, Direct Tablet Grade: 212.0 grams The active ingredient was thoroughly blended in a suitable mixer with the tablet excipients and compressed on a single punch tablet machine into 1,000 tablets, each weighing 300 mg. and containing 20 mg. of the psoralen compound, i.e., 8-methoxypsoralen, as active ingredient.

EXAMPLE 3

Gelatin Capsule Formulation — Psoralen

Psoralen Compound, fine powder: 20.4 grams
Corn Starch, USP: 194.6 grams

The active ingredient was thoroughly mixed with starch and filled into 1,000 #3 two-piece hard gelatin capsules, each capsule containing 220 mg. of the mixture, which represents 20 mg. of the active ingredient per capsule.

EXAMPLE 4

Solution Formulation — Psoralen

Psoralen Compound: 1.02 grams
Butylated Hydroxytoluene (BHT): 0.01 gram
Acetone: 20.0 ml.
Propylene Glycol: 5.0 ml.
Ethanol 95%, enough to make: 100 ml.

The active ingredient was dissolved in a 50 ml. mixture of ethanol (25 ml.)/acetone (20 ml.)/propylene glycol (5.0 ml.) in a flask heated on a water bath, the BHT (antioxidant) was added and dissolved, then the solution allowed to cool to room temperature at which time the ethanol was added to make the final volume 100 ml.

EXAMPLE 5

Ointment Formulation — Psoralen

Psoralen Compound, Micronized: 10.0 grams
Hydrophilic Petrolatum USP qs. ad: 1000 grams To 990 grams of hydrophilic petrolatum melted on a steam bath, the active ingredient was added with constant stirring until uniformly dispersed. The mixture was removed from the steam bath and stirred constantly until the ointment congealed. The final product may be put through a roller mill to insure adequate dispersion of the active ingredient.

EXAMPLE 6

Manufacture of a capsule filling material of the following composition:
9-(4-methoxy-2,3,6-trimethylphenyl)-3,7-dimethylnona-2,4,6,8-tetraen-1-oic acid ethyl ester: 0.1 g.
Wax mixture: 51.4 g.
Vegetable oil: 103.0 g.
Trisodium salts of ethylenediamine tetraacetic acid: 0.5 g.
Individual weight of a capsule: 150.0 mg.
Active material content of a capsule: 10.0 mg.

EXAMPLE 7

Manufacture of a water/fat emulsion containing 0.3% active material of the following composition:
9-(4-methoxy-2,3,6-trimethylphenyl)-3,7-dimethylnona-2,4,6,8-tetraen-1-oic acid ethyl amide: 0.3 g.
Magnesium stearate: 2.0 g.
Perhydrosqualene: 13.0 g.
Water: qs to 100 ml.

I claim:

1. An improved method for treating a psoriatic subject undergoing treatment with a psoralen in conjunction with ultraviolet A radiation of from wavelength of 3200 to 4000 angstroms, which improved method comprises
   prior to initiation of said treatment, pretreating said subject for a period of from 4 to 10 days with an effective amount of an anti-psoriatic polyene compound, and thereafter
   initiating said treatment with a psoralen in conjunction with ultraviolet A radiation and continuing said treatment concurrently with the administration of said anti-psoriatic polyene compound.

2. The method of claim 1 wherein said pretreatment is for a period of 7 days prior to initiation of treatment with a psoralen in conjunction with ultraviolet A radiation.

3. The method of claim 2 wherein said polyene compound is a retinoid.

4. The method of claim 3 wherein said retinoid is an all-trans-9-(4-methoxy-2,3,6-trimethylphenyl)-3,7-dimethyl-2,4,6,8-nonatetrene-1-oic acid ester.

5. The method of claim 4 wherein said retinoid is ethyl all-trans-9-(4-methoxy-2,3,6-trimethylphenyl)-3,7-dimethyl-2,4,6,8-nonatetraenoate.

6. The method of claim 5 wherein said ethyl all-trans-9-(4-methoxy-2,3,6-trimethylphenyl)-3,7-dimethyl-2,4,6,8-nonatetraenoate is provided by enteral administration in daily doses in the range of 5-200 mg.

7. The method of claim 3 wherein said retinoid is administered on a daily basis.

8. The method of claim 3 wherein said retinoid is administered 1 to 3 times weekly.

9. In a method for treating psoriasis by administering to a psoriatic subject a psoralen compound in conjunction with ultraviolet A radiation of from wavelength of 3200 to 4000 angstroms, the improvement comprising concurrently administering to said subject an effective amount of an anti-psoriatic polyene compound.

10. The method of claim 9, wherein said polyene compound is a retinoid.

11. The method of claim 10 wherein said retinoid is ethyl all-trans-9-(4-methoxy-2,3,6-trimethylphenyl)-3,7-dimethyl-2,4,6,8-nonatetraenoate.

12. The method of claim 11 wherein said ethyl all-trans-9-(4-methoxy-2,3,6-trimethylphenyl)-3,7-dimethyl-2,4,6,8-nonatetraenoate is provided by enteral administration in daily doses in the range of 5-200 mg.

* * * * *